United States Patent [19]

Blaisdell et al.

[11] Patent Number: 4,698,438

[45] Date of Patent: Oct. 6, 1987

[54] PROCESS FOR THE PREPARATION OF METHYL CARBAMATES AND THIOIMIDATES

[75] Inventors: Charles T. Blaisdell, Middletown; Walter J. Cordes, Wilmington, both of Del.; George E. Heinsohn, Elkton, Md.; John F. Kook, Hockessin; John R. Kosak, Greenville, both of Del.

[73] Assignee: E. I. Du Pont de Nemours and Company, Wilmington, Del.

[21] Appl. No.: 827,517

[22] Filed: Feb. 11, 1986

Related U.S. Application Data

[63] Continuation-in-part of Ser. No. 727,812, Apr. 26, 1985.

[51] Int. Cl.$^4$ .................. C07C 119/18; C07C 131/00; C07C 125/04; C07D 307/78
[52] U.S. Cl. ......................................... 558/3; 564/255; 560/134; 560/132; 560/338; 549/470; 549/452; 549/438
[58] Field of Search ............................ 558/3; 564/255; 560/134, 132, 338; 549/470, 452, 438

[56] References Cited

U.S. PATENT DOCUMENTS

| | | | |
|---|---|---|---|
| 2,870,057 | 1/1959 | Hartle et al. | 560/134 |
| 3,506,698 | 4/1970 | Jelinek | 558/3 |
| 3,576,834 | 4/1971 | Buchanan | 558/3 |
| 4,207,251 | 6/1980 | Heyboer | 558/3 |

FOREIGN PATENT DOCUMENTS

56-100751 8/1981 Japan .......................... 558/3

*Primary Examiner*—John M. Ford
*Assistant Examiner*—Robert C. Whittenbaugh
*Attorney, Agent, or Firm*—James A. Costello

[57] ABSTRACT

A continuous, close-coupled method for making N-methyl carbamate pesticides which comprises contacting the methyl isocyanate in a vapor phase mixture containing methyl isocyanate and water with a selected oxime or phenol, said mixture being the reaction product formed by oxidizing monomethylformamide. An optional intermediate step for preparing the methyl isocyanate/water vapor phase reaction mixture for contact with the oxime or phenol is to remove therefrom a portion of the water without liquefying the methyl isocyanate by cooling the mixture to a temperature below the dew point of water but above the dew point of the methyl isocyanate.

45 Claims, No Drawings

PROCESS FOR THE PREPARATION OF METHYL CARBAMATES AND THIOIMIDATES

CROSS-REFERENCE TO RELATED APPLICATION

This application is a continuation-in-part of copending application bearing U.S. Ser. No. 727,812, filed Apr. 26, 1985.

BACKGROUND OF THE INVENTION

This invention concerns a process for manufacturing pesticides from methyl isocyanate (MIC) in which the MIC is generated as a gas and consumed in a close-coupled reactor column so that very little MIC is present at any time. The use of MIC to manufacture pesticides is known, but all of the known methods involve storing and handling liquid MIC. This is dangerous because MIC is extremely toxic and very reactive (even with water) in liquid form. By the method of this invention, a gaseous stream containing MIC and water, typically one generated by controlled oxidative dehydrogenation of relatively nontoxic nonreactive monomethylformamide (MMF), is passed into a column reactor where the MIC reacts with an oxime or phenol to form the carbamate.

Heretofore, prior art methods directed to minimizing intermediate reactions of the MIC/water formed by oxidizing MMF featured various methods of physically separating the MIC from the water. Such methods typically involved the intermediate isolation and storage of MIC preparatory to its reaction with the oxime or phenol to form the desired pesticide. The process of this invention eliminates the need for storing MIC with the consequent risk. The MIC is contacted with the oxime or phenol continuously as the MIC is being made, in the vapor phase, in a closed system.

U.S. Pat. No. 3,576,834 discloses certain N-methyl carbamates and their preparation by the reaction of an oxime with methyl isocyanate (MIC) in an aprotic solvent. The MIC used in that method can be prepared in a variety of ways, one of which is the gas phase reaction of N-methylformamide with oxygen, as shown in U.S. Pat. No. 4,207,251. That patent discloses physical separation of the water and MIC to avoid reaction between the MIC and the water. Japanese Kokai 56/100751 discloses a process for making MIC from monomethylformamide and that the water by-product of the reaction can be separated from the MIC by ordinary distillation.

U.S. Pat. No. 3,506,698 discloses making certain N-methyl carbamates by contacting an oxime with MIC in a reaction medium that comprises at least 50% water. The disclosed reaction takes place in the liquid phase. In several Examples, the reactants are added to water and the reaction mass is cooled, apparently to insure reaction within the preferred temperature range of 20° to 60° C.

U.S. Pat. No. 4,207,251 describes the problem caused by reaction between various isocyanates and water produced by oxidation of formamides. The disclosed solution is to physically separate the isocyanate and water to prevent them from reacting. Disclosed separation methods include filtration, extraction, use of molecular sieves, water-absorbing agents or a water-immiscible solvent for the isocyanate. This patent is silent concerning conditions under which isocyanates are reacted to form pesticides.

SUMMARY OF THE INVENTION

This invention concerns an improved process for forming a pesticide by reacting methyl isocyanate with an oxime or phenol selected from the group

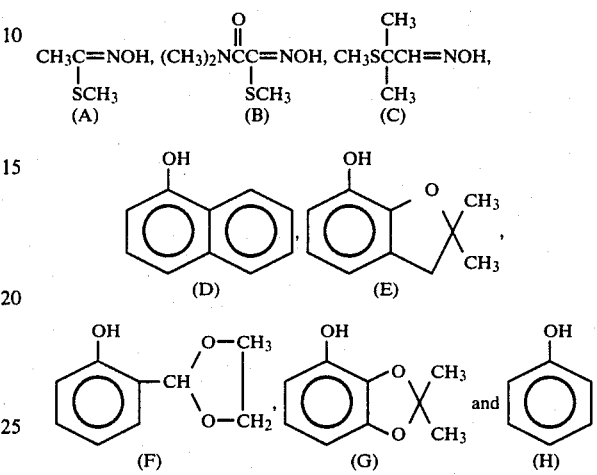

the improvement comprising:
(i) employing as the source of methyl isocyanate, the reaction mixture formed from the oxidative dehydrogenation of monomethylformamide, said reaction mixture containing methyl isocyanate and water in the vapor phase,
(ii) contacting the phenol or oxime with the methyl isocyanate described in (i) in a continuous, close-coupled process employing one of steps (iii) or (iv) to prepare the methyl isocyanate for contact with the oxime or phenol,
(iii) maintaining the temperature of the methyl isocyanate/water vapor phase mixture between about 100° C. to 650° C. until the time of contact,
(iv) enriching the mixture in methyl isocyanate relative to water by diluting with inert gas and cooling to preferentially condense water rather than methyl isocyanate.

Both of alternative steps (iii) and (iv) are characterized by providing, to the oxime- or phenol-contacting-step (ii), MIC substantially as produced by MMF oxidative dehydrogenation without significant loss attributable to MIC-water reaction. Thus, both steps provide MIC reactant uncontaminated by significant amounts of dimethylurea (DMU) formed by reaction of MIC and water. Step (iv) is also characterized in that high boiling materials and other unwanted byproducts of the MMF oxidation, including DMU, are removed along with the major portion of the water.

The preferred method for removing a portion of the water in step (iv) is by partial condensation of water from the MIC/water mixture without liquefying the MIC and without interrupting the continuity of the close-coupled process. The partial condensation is effected by cooling the mixture to a temperature below the dew point of the water but above the dew point of the methyl isocyanate and separating the condensed phase of water and high boiling impurities from the methyl isocyanate. When this alternative preparation step is employed, the partial condensation step is preferably operated so that the mole ratio of MIC to water in the effluent stream is at least about 3; most preferably, the ratio will be at least about 5.

MIC vapor reacts with liquid water at a rate that is temperature-dependent and appreciable above about 30°. To minimize loss, the liquid phase in the condenser should be kept below this temperature since it is mostly water. The freezing point of water sets a lower limit of about 0°; best results are achieved by operating the condenser at 0° to 20° C. The temperature at which MIC will condense as a separate liquid phase is a function of the mole fraction of MIC in the gaseous phase; the lower the proportion of MIC, the lower the temperature required to condense MIC (the "MIC dew point" as defined hereafter). If the gas stream is not diluted with $N_2$, the condenser would have to be operated at relatively high temperature to avoid condensing MIC and this would lead to accelerated reaction in the condenser between gaseous MIC and liquid water. Sufficient $N_2$ is added to the gas stream to allow the desired cooling without condensing liquid MIC. The $N_2$ may be added prior to step (i) to aid in temperature control during the oxidative dehydrogenation of monomethylformamide.

DETAILS OF THE INVENTION

Definitions And Characterization

By "close-coupled" is meant that substantially all the MIC formed in an earlier stage of the process is consumed in reaction with the oxime or phenol within a very short time of the MIC formation. The residence time for the MIC before it is consumed is typically of the order of 10 seconds or less. Higher residence times are possible but may result in increased MIC yield loss.

By "dew point" as employed herein with regard to MIC is meant the temperature at or below which MIC vapor condenses at a rate sufficient to form a separate liquid MIC phase. The MIC dew point will vary, depending on the composition of the gas-phase mixture itself, but it can be readily calculated by available methods. In this regard, diluent gas volume will have an important effect on dew point. The dew point of MIC is controlled by dilution with inert gas, e.g., nitrogen, so that the condensation can be performed within the temperature range of about 0° to 30° C.

The process of this invention is characterized in that: (a) MIC is present only as a transient intermediate since it is formed and consumed in a close-coupled process; (b) the total mass of MIC is kept at a minimum by low total residence time and use of a diluent gas; (c) liquefaction of potentially unstable MIC is avoided; (d) MIC yield losses are minimized; and (e) high purity products substantially free of phytotoxic materials are produced when partial condensation is employed as the optional separation step.

Steps (i), (ii) and (iii)

The MMF to MIC reaction can be accomplished in a close-coupled gas phase reaction in which the gaseous feed to the reactor contains MMF, oxygen (air), and diluent nitrogen. Recycled process gas also can be used as a diluent. Nitrogen is preferred. The diluent gas is used to cool the catalyst as well as to optimize the partial condensing step. Typical catalysts and operating conditions of these reactors are described in U.S. Pat. Nos. 4,207,251 and 4,537,726. The reaction described in those patents generates a gas phase mixture of inert gas, water, MIC, unreacted MMF and several by-products.

It has been found advantageous for all the reasons described above to contact the oxime or phenol with the gaseous effluent from the MMF-to-MIC oxidation process. The reaction is carried out continuously at a temperature typically maintained between about 0° to 70° C. and preferably between about 15° to 50° C. The amount of water in the vapor phase that contacts the oxime or phenol is determined by the composition of the effluent exiting the MMF-to-MIC oxidation step and is no greater than about 50 mole percent based on MIC and water in the effluent.

Steps (i), (ii) and (iv)

Alternatively, the MIC/water reaction mixture can be subjected to partial condensation before contacting the oxime or phenol. The MIC/water reaction mixture will contain some small amount of unreacted MMF and other high boiling, e.g., above 80° C., materials that can be liquefied and removed from the gas stream, without also liquefying the MIC, by controlled cooling with optional adjustment of pressure of the gas-phase reaction product mixture. The mixture is cooled to a temperature sufficiently low to condense the water vapor but above the dew point of MIC in the mixture. A shell-and-tube type condenser with glass bead packing has been employed. The glass bead packing promotes coalescence of water droplets and high boiling impurities and further minimizes residence time.

In general, it is preferred to cool the gas mixture to a temperature about 5 to 10 degrees Celsius above the MIC dew point. In this context, good results are obtained when the MIC dew point is lowered by dilution with nitrogen so that the gas mixture can be cooled to about 0° to 30° C., with operation preferred at 0° to 20° C. (at atmospheric pressure). An additional method for bringing the dew point of MIC into the desired range is by varying the system pressure. Difficulties attendant upon that expedient render it less desirable than nitrogen dilution as the means for controlling MIC dew point.

The MIC removal (from the diluent gas) is accomplished in a reactor which ensures good gas-liquid contact. Conventional packed, sieve tray, and bubble cap reactor columns are all acceptable. Other reactors contemplated for use include those employing permeators, absorber and membrane principles for improving good contact between the MIC and the oxime or phenol. Greater than 99% reaction of MIC is achievable in one or more reaction stages under preferred conditions.

Solvent

The organic liquid used as the solvent can be any in which the oxime or phenol dissolves or partially dissolves and is preferably but not necessarily immiscible with water. Contemplated solvent media for the oxime or phenol include one or a mixture of toluene, dimethylformamide, xylene, cyclohexanone, methylisobutylketone or a chlorinated hydrocarbon such as methylene chloride, chloroform, mono- and dichlorobenzene and the like. It may sometimes be preferred, for instance when the phenol reactant is phenol H, not to employ a solvent.

The most preferred solvent for oxime (A) is methylene chloride. For best results, the oxime and the gas mixture of MIC/water are combined in countercurrent flow. If product or oxime solubility in the solvent prevents the use of countercurrent contact, then, just the solvent is contacted with the MIC gas stream in a countercurrent mode while the oxime is added to the bottom of the reactor. It has been found most advantageous if the process is operated at water concentration in the gas phase mixture of between about 1 to 30 mole percent of the MIC that is present. The N-methylcarbamates made by the process of this invention are characterized by being substantially free of monomethylformamide and/or dimethylurea contamination.

A basic catalyst such as triethylamine (TEA) or triethylenediamine can be added to the solvent to speed up the reaction or improve selectivity although it is usually not necessary. The selected solvent will be inert to MIC and will have effective reactant and product solubility as well as volatility. The column can be operated in the continuous mode or sequential batch mode. The oxime or phenol can enter above the MIC gas feed point or below. If the oxime or phenol is added below the feed point the solvent is added above the feed point to absorb MIC for reaction with the oxime or phenol. The liquid from the base of the column can be recycled. The process of this invention continuously consumes reactant MIC in one reactor or in several reactors operated intermittently, serially or concurrently.

Heat can be applied to increase the rate of reaction, aid in the absorption of MIC by refluxing condensed solvent or control the solvent balance and prevent precipitation of product and intermediates. The preferred operating temperatures depend on product/intermediate solubility and solvent. Usually 15° to 50° C. in methylene chloride gives a sufficient rate of reaction between MIC and the oxime or phenol while minimizing the reaction with water. Near stoichiometric ($\pm 10\%$) feeds of oxime/phenol and MIC are preferred to efficiently remove the hazardous MIC from the vent gas and conserve the oxime/phenol feedstock. The noncondensable vent gas is ejected through standard equipment to render the vent environmentally acceptable or recycled as a diluent gas. The product solution can be used as is or further refined.

The pesticide is removed from the reactor as a solution or slurry in the solvent used and possibly mixed with water for further purification or refining. If the mixture separates into two phases, organic and aqueous, the phases can be separated easily by decantation or filtration. If there is only one phase, the product can be separated by well known chemical engineering methods such as crystallization or fractional distillation, and purified by techniques well known in the art.

The following Examples illustrate the process of this invention.

EXAMPLE 1

According to the procedure described in U.S. Pat. No. 4,537,726, to a reactor (reactor 1) was fed 0.63 g/min of MMF, 377 cc/min of $N_2$ and 344 cc/min of air. To a second reactor (reactor 2) was fed an additional 352 cc/min air. Reactor 1 temperature was 550° C. Reactor 2 temperature was 580° C. The partial condenser exit temperature was 2° C. with a condensation rate of 0.33 grams of condensate per g of MMF fed to reactor 1. Analysis of the partial condenser exit gas showed 2.8 mole percent of $CO_2$ and 14.1 mole percent of MIC. To the top of the column was fed 3.58 g/min of 22.9% of methyl N-hydroxythioacetimidate (A) and 1% $H_2O$ in methylene chloride. Product was removed from the column continuously at 2.88 g/min with a conversion to the desired methomyl of 88%. MIC removal from the gas was 99+%. Column temperature was maintained at 20° to 30° and pot temperature kept at 51° C.

EXAMPLES 2 to 5

Substantially no water is present in the MIC mixtures of Examples 2 through 5. Nevertheless, said Examples demonstrate the manner in which MIC would react with oximes A and B and phenol E in step (ii) of a step (i)/(ii)/(iv) process.

EXAMPLE 2

A mixture of gaseous MIC (0.94 g/min) and $N_2$ (2.4 L/min) was fed to the base of a 2 foot high, one inch diameter, 10 plate sieve glass column (4—5 theoretical stages) above a heated 50 mL volume of methylene chloride. The unreacted vent gas passed through a condenser where methylene chloride was condensed and returned to the top of the column. A liquid feed of 14.2 g/min of 15% by weight of methyl N-hydroxythioacetimidate (A) and 0.8% of triethylamine in methylene chloride was fed to the top of the packed section and flowed countercurrent to the gas. Sufficient heat was applied to maintain a column temperature of 21° C. (base temperature of 45° C.). MIC removal from the gas was 99.7% and the product accumulated over a one hour period of time was 81.9% converted to methomyl.

EXAMPLE 3

To the same apparatus employed in Example 2 was fed 1.0 g/min of gaseous MIC and 2.4 L/min of $N_2$. To the top of the column was fed a 11.7 g/min liquid feed of 26% methyl N-hydroxythioacetimidate (A) containing 1% $H_2O$, 4% impurities, and the balance methylene chloride. The column temperature was maintained at 21° C. by refluxing methylene chloride and the product withdrawn continuously from the bottom. After three hours of continuous operation the vent gas was 99+% free of MIC and the product stream contained 10.2% of N-hydroxythioacetimidate (A) and 17.0% methomyl. Mass balance calculations show a MIC/N-hydroxythioacetimidate feed mole ratio of 0.54 and a product methomyl/(methomyl+N-hydroxythioacetimidate) mole ratio of 0.51. Thus, there is a good accounting of the MIC to methomyl reaction and a minimal loss of MIC to reaction with water or other impurities.

EXAMPLE 4

To the apparatus of Example 2 was fed 1.10 g/min of gaseous MIC and 2.4 L/min of $N_2$. To the heated pot below the column was fed 9.75 g/min of a 40% slurry of methyl 2-(dimethylamino)-N-hydroxy-2-oxoethanimidothioate (B) in methylene chloride. To the top of the column was fed 10 g/min of methylene chloride. The column temperature was maintained at 19° C. (base at 53° C.) with refluxing methylene chloride. After a feed period of 40 minutes the pot contained 27% of oxamyl and no detectable methyl 2-(dimethylamino)-N-hydroxy-2-oxoethanimidothioate. The MIC removal efficiency from the gas was 99%.

EXAMPLE 5

To the apparatus of Example 2 was added 1.0 g/min of gaseous MIC and 2.4 L/min of $N_2$. To the top of the column was added 10 g/min of 15% of 2,3-dihydro-2,2-dimethyl-7-hydroxybenzofuran (E) in methylene chloride with 1.0% of triethylamine catalyst. The column top temperature was maintained at 20° C. The product slurry formed in the pot was 38.4% carbofuran. Vent gases were 99% free of MIC. Without triethylamine, the same experiment gave 70% conversion to product.

EXAMPLE 6

In the manner described in Example 1, the pesticide aldicarb can be made by contacting 2-methyl-2-(methylthio)propanal oxime (C) with MIC.

EXAMPLE 7

In the manner described in Example 1, N-methylcarbamoyloxy-2-(1,3-dioxolan-1-yl)benzene can be made by contacting 2-(1,3-dioxolan-1-yl)phenol (F) with MIC.

EXAMPLE 8

In the manner described in Example 1, the pesticide bendiocarb can be made by contacting 2,2-dimethyl-1,3-benzodioxol-4-ol (G) with MIC.

EXAMPLE 9

Liquid N-methylformamide was fed to a vaporizer at the rate of 2 cc per minute along with air at the rate of 1870 standard cubic centimeters per minute. The vaporizer was maintained at 225°±25° C. The vapor mixture was fed to a reactor containing 8 g of granular silver catalyst set into a fluidized sand bath held at 450° C. The temperature of the catalyst bed began to rise almost immediately and stabilized at 600°±10° C. Based on gas chromatography analyses of the reaction product stream from the silver catalyst reactor, conversion of N-methylformamide to methyl isocyanate was about 85%. The stream contained an average of 5%, by weight, of water.

The gas stream was fed forward to a second reactor where it came in contact with a solution of 50 g of 1-(methylthio)acetaldoxime in one liter of dimethylformamide. The dimethylformamide solution was fed countercurrent to the flow of vapor through a column packed with glass beads. The oxime reactor was cooled to maintain the temperature of the solution in the range of 20° to 50° C. The product solution was fed to a pump reservoir which, in turn, recycled the solution to the top of the oxime reactor. The solution was recycled until all of the oxime was consumed. After one hour, the DMF solution was found by high pressure liquid chromatography to contain methomyl.

EXAMPLE 10

Methyl isocyanate was prepared as in Example 9 except that the sand bath temperature was maintained at 375° C. and the catalyst bed stabilized at 640°±10° C. The gas stream was passed through a partial condenser and the MIC effluent was contacted with a solution of α-naphthol (D) in dimethylformamide. The pesticide, carbaryl, precipitated from solution at 93.5% purity.

EXAMPLE 11

Methyl isocyanate was prepared as in Example 10 except that the sand bath was held at 450° C. and the catalyst bed stabilized at 535°±10° C. After being passed through a partial condenser, the MIC-enriched effluent was contacted with molten phenol containing a small amount of triethylenediamine. The yield of phenyl methylcarbamate pesticide was 90.5%.

The embodiments of the invention in which an exclusive property or privilege is claimed are defined as follows:

1. In a process for forming an insecticide by reacting methyl isocyanate with an oxime or phenol selected from the group

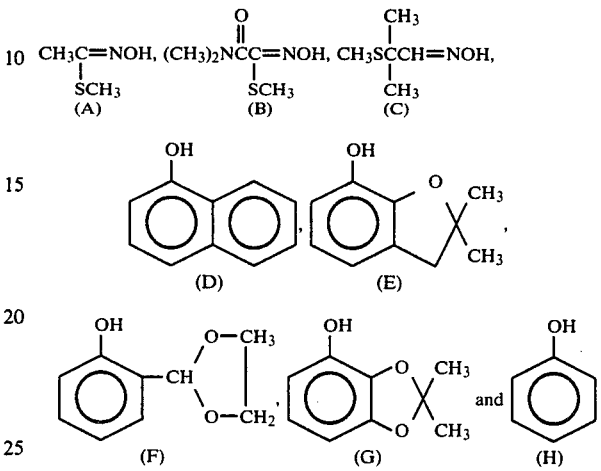

the improvement comprising:
(i) employing as the source of methyl isocyanate, the reaction mixture formed from the oxidative dehydrogenation of monomethylformamide, said reaction mixture containing methyl isocyanate and water in the vapor phase,
(ii) contacting the oxime or phenol with the methyl isocyanate described in (i) in a continuous, close-coupled process employing one of steps (iii) or (iv) to prepare the methyl isocyanate for contact with the oxime or phenol,
(iii) maintaining the temperature of the methyl isocyanate/water vapor phase mixture between about 100° C. to 650° C. until the time of contact,
(iv) enriching the mixture in methyl isocyanate relative to water by diluting with inert gas and cooling to preferentially condense water rather than methyl isocyanate.

2. A process according to claim 1 employing steps (i), (ii) and (iii).

3. A process according to claim 1 employing steps (i), (ii) and (iv).

4. A process according to claim 3 wherein step (iv) comprises cooling the MIC/water mixture to a temperature below the dew point of the water but above the dew point of the MIC, condensing a portion of the water and high boiling impurities from step (i), and separating the condensed phase from the methyl isocyanate.

5. A process according to claim 1 employing oxime A.

6. A process according to claim 2 employing oxime A.

7. A process according to claim 3 employing oxime A.

8. A process according to claim 4 employing oxime A.

9. A process according to claim 1 employing oxime B.

10. A process according to claim 2 employing oxime B.

11. A process according to claim 3 employing oxime B.

12. A process according to claim 4 employing oxime B.

13. A process according to claim 1 employing oxime C.

14. A process according to claim 2 employing oxime C.

15. A process according to claim 3 employing oxime C.

16. A process according to claim 4 employing oxime C.

17. A process according to claim 1 employing phenol D.

18. A process according to claim 2 employing phenol D.

19. A process according to claim 3 employing phenol D.

20. A process according to claim 4 employing phenol D.

21. A process according to claim 1 employing phenol E.

22. A process according to claim 2 employing phenol E.

23. A process according to claim 3 employing phenol E.

24. A process according to claim 4 employing phenol E.

25. A process according to claim 1 employing phenol F.

26. A process according to claim 2 employing phenol F.

27. A process according to claim 3 employing phenol F.

28. A process according to claim 4 employing phenol F.

29. A process according to claim 1 employing phenol G.

30. A process according to claim 2 employing phenol G.

31. A process according to claim 3 employing phenol G.

32. A process according to claim 4 employing phenol G.

33. A process according to claim 1 employing phenol H.

34. A process according to claim 2 employing phenol H.

35. A process according to claim 3 employing phenol H.

36. A process according to claim 4 employing phenol H.

37. A process according to claim 5 wherein the oxime or phenol and methyl isocyanate are contacted in countercurrent flow.

38. A process according to claim 9 wherein the oxime or phenol and methyl isocyanate are contacted in countercurrent flow.

39. A process according to claim 13 wherein the oxime or phenol and methyl isocyanate are contacted in countercurrent flow.

40. A process according to claim 17 wherein the oxime or phenol and methyl isocyanate are contacted in countercurrent flow.

41. A process according to claim 21 wherein the oxime or phenol and methyl isocyanate are contacted in countercurrent flow.

42. A process according to claim 25 wherein the oxime or phenol and methyl isocyanate are contacted in countercurrent flow.

43. A process according to claim 29 wherein the oxime or phenol and methyl isocyanate are contacted in countercurrent flow.

44. A method according to claim 7 wherein the mole ratio of MIC to water is at least about 3.

45. A method according to claim 8 wherein the mole ratio of MIC to water is at least about 3.

* * * * *